(12) United States Patent
Zhang et al.

(10) Patent No.: US 7,378,539 B2
(45) Date of Patent: *May 27, 2008

(54) COMPOUND, A MOLECULAR SWITCH EMPLOYING THE COMPOUND AND A METHOD OF ELECTRONIC SWITCHING

(75) Inventors: Sean X. Zhang, Sunnyvale, CA (US); Zhang-Lin Zhou, Mountain View, CA (US); Kent Vincent, Cupertino, CA (US); R. Stanley Williams, Portola Valley, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 360 days.

This patent is subject to a terminal disclaimer.

(21) Appl. No.: 10/946,288

(22) Filed: Sep. 22, 2004

(65) Prior Publication Data

US 2006/0060837 A1   Mar. 23, 2006

(51) Int. Cl.
*C07F 9/02* (2006.01)
(52) U.S. Cl. .......................... 558/190; 558/286; 560/8
(58) Field of Classification Search ................ 558/190, 558/286; 560/8
See application file for complete search history.

(56) References Cited

U.S. PATENT DOCUMENTS

2002/0110831 A1   8/2002   Schlag
2002/0158243 A1   10/2002  Schlag
2002/0158244 A1   10/2002  Schlag
2004/0138467 A1   7/2004   French et al.
2006/0060836 A1*  3/2006   Zhang et al. ................. 257/40

FOREIGN PATENT DOCUMENTS

WO   WO 02/080290 A   10/2002
WO   WO 02/089229 A   11/2002

OTHER PUBLICATIONS

Smith, M. B.; March, J. March's Advanced Organic Chemistry, 5th ed.; John Wiley & Sons, Inc.: New York, 2001; pp. 46-71.

* cited by examiner

*Primary Examiner*—Rei-tsang Shiao

(57) ABSTRACT

Classes of molecules are disclosed which can, for example, be used in molecular switches. The classes of molecules include at least three segments—an electronic donor ("D"), a switchable bridge ("B"), and an electronic acceptor ("A")—chemically connected and linearly arranged (e.g., D-B-A). The electronic donor can be an aromatic ring system with at least one electron donating group covalently attached; an aromatic ring system with an electron withdrawing group covalently attached is usually employed as the electronic acceptor; and the switchable bridge can be a pi system that can be switched on or off using an external electric field.

8 Claims, 8 Drawing Sheets

COMPOUND, A MOLECULAR SWITCH EMPLOYING THE COMPOUND AND A METHOD OF ELECTRONIC SWITCHING

BACKGROUND

Molecular scale electronics, including molecular rectifiers, is an active area of research. A simple electronic device constructed out of a single organic molecule, such as a rectifier, can consist of a donor π-system and an acceptor π-system separated by a sigma-bonded methylene bridge. Semiquantitative calculations can be performed on a hemiquinone to support the concept.

Molecular electrical rectification can also be observed in Langmuir-Blodgett multilayers or monolayers of γ-hexadecylquinolinium tricyanoquino-dimethanide sandwiched between metallic electrodes. However, the mechanism of rectification is not necessarily the donor-insulator-acceptor mechanism. Rather, the envisioned insulator (i.e., sigma-bonded methylene bridge) does not sufficiently isolate the donor pi system from the acceptor pi system.

SUMMARY

A compound is disclosed having a structure:

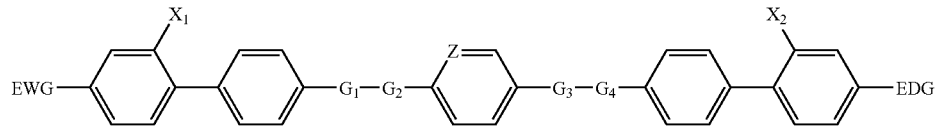

wherein "EWG" is selected from a group consisting of —C(=O)H, —C(=O)$R_3$, —C(=O)O$R_3$, —C(=O)OH, —CN, —N=O, —$NO_2$, —$SO_2$OH, —N=N—, CH=$NR_3$, —$CR_3$=$NR_4$, —C=C(CN)$_2$, —C=C(COR$_3$)$_2$, —C=C(CO$_2$R$_3$)$_2$, —C=C(COR$_3$)CO$_2$R$_4$, —SO$_2$OR$_3$, —S(=O)—R$_3$, —SO$_2$R$_3$, —BH$_2$, —BHR$_3$, —BR$_3$R$_4$, —PO$_3$H$_2$, —PO$_3$R$_3$R$_4$, wherein $R_3$ and $R_4$ are substituents independently selected from linear alkyl, branched alkyl, cyclic alkyl, and an aromatic ring system, and wherein the alkyl substituents are substituted or unsubstituted. "EDG" is selected from a group consisting of —O—, —OH, —OR$_1$, —NH—, —NH$_2$, —NHR$_1$, —NR$_1$R$_2$, —PR$_1$R$_2$, —PHR$_1$, —S—, —SH, —SR$_1$, F, Cl, Br, and I, wherein R$_1$ and R$_2$ are substituents independently selected from linear alkyl, branched alkyl, cyclic alkyl, and an aromatic ring system, and wherein the alkyl substituents are substituted or unsubstituted. X$_1$ and X$_2$ are independently selected from a group consisting of hydrogen, F, Cl, Br, and I, —OH, —SH, —NH$_2$; and substituted alkyl groups. G$_1$-G$_2$ and G$_3$-G$_4$ are independently selected from a group consisting of —CH=CH—, —CH=CR$_5$—, —CR$_5$=CR$_6$—, —CH$_2$C(=O)—, —CR$_5$HC(=O)—, —CC—, —N=N—, —N=CH—, —NH—CO—, —N=C(NH$_2$)—, —N=C(SH)—, —NCS—, —NH—O— and —NHNH—, wherein R$_5$ and R$_6$ are substituents independently selected from linear alkyl, branched alkyl, cyclic alkyl, and an aromatic ring system, and wherein the alkyl substituents are substituted or unsubstituted. Z is selected from a group of atomic units consisting of —CH=, —N=, —S—, —O—, and —P=.

A compound is also disclosed having a structure:

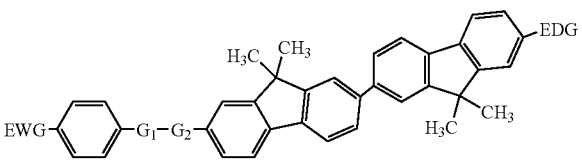

wherein "EWG" is selected from a group consisting of —C(=O)H, —C(=O)$R_3$, —C(=O)O$R_3$, —C(=O)OH, —CN, —N=O, —NO$_2$, —N=N—, CH=NR$_3$, —CR$_3$=NR$_4$, —C=C(CN)$_2$, —C=C(COR$_3$)$_2$, —C=C(CO$_2$R$_3$)$_2$, —C=C(COR$_3$)CO$_2$R$_4$, —SO$_2$OH, —SO$_2$OR$_3$, —S(=O)—R$_3$, —SO$_2$R$_3$, —BH$_2$, —BHR$_3$, —BR$_3$R$_4$, —PO$_3$H$_2$, —PO$_3$R$_3$R$_4$, wherein $R_3$ and $R_4$ are substituents independently selected linear alkyl, branched alkyl, cyclic alkyl, and an aromatic ring system, and wherein the alkyl substituents are substituted or unsubstituted. "EDG" is selected from a group consisting of —O—, —OH, —OR$_1$, —NH—, —NH$_2$, —NHR$_1$, —NR$_1$R$_2$, —PHR$_1$, —PR$_1$R$_2$, —S—, —SH, —SR$_1$, F, Cl, Br, and I, wherein R$_1$ and R$_2$ are substituents independently selected from linear alkyl, branched alkyl, cyclic alkyl, and an aromatic ring system, and wherein the alkyl substituents are substituted or unsubstituted. G$_1$-G$_2$ is selected from a group consisting of —CH=CH—, —CH=CR$_5$—, —CR$_5$=CR$_6$—, —CH$_2$C(=O)—, —CR$_5$HC(=O)—, —CC—, —N=N—, —N=CH—, —NH—CO—, —N=C(NH$_2$)—, —N=C(SH)—, —NCS—, —NH—O— and —NHNH—, wherein R$_5$ and R$_6$ are substituents independently selected from linear alkyl, branched alkyl, cyclic alkyl, and an aromatic ring system, and wherein the alkyl substituents are substituted or unsubstituted.

A molecular diode switch is disclosed which includes a compound of a structure D-B-A, wherein "D" is an electronic donor, "B" is a switchable bridge, and "A" is an electronic acceptor; and two electrodes in operable contact with the compound.

A disclosed method of electronic switching includes applying an electric field of a first polarity to a compound, wherein the compound is of a structure D-B-A, and wherein "D" is an electronic donor, "B" is a switchable bridge, and "A" is an electronic acceptor, to cause a first conformational change in the compound that allows electron conductance through the compound's π-system; and applying an electric field of a second, opposite polarity to the compound, thereby causing a second conformational change in the compound that inhibits electron conductance through the compound's pi system.

BRIEF DESCRIPTION OF THE DRAWINGS

The following detailed description of preferred embodiments can be read in connection with the accompanying drawings in which like numerals designate like elements and in which.

DETAILED DESCRIPTION

Figure 1:
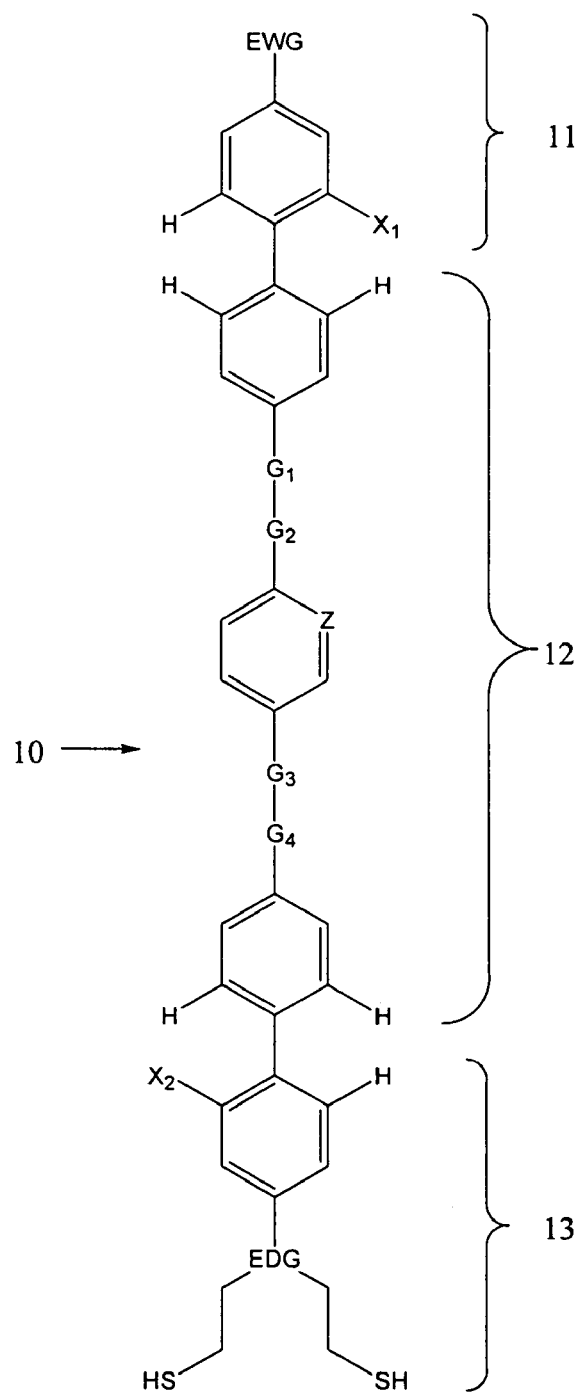
FIG. 1 shows an exemplary subclass of molecules disclosed herein.

Classes of molecules are disclosed herein that can be employed in molecular switches. Molecular switches containing the molecule classes, and methods of electronic switching using the molecule classes are also disclosed.

Exemplary classes of molecules disclosed herein include a molecule having at least three segments—an electronic donor ("D"), a switchable bridge ("B"), and an electronic acceptor ("A")—chemically connected and linearly arranged (e.g., to form a compound of the structure D-B-A). The electronic donor can be an aromatic ring system with at least one electron donating group covalently attached; an aromatic ring system with an electron withdrawing group covalently attached can be employed as the electronic acceptor; and, the switchable bridge can be a π-system that can be switched on or off using an external electric field.

The bridge can be switched "on" by inducing a change in the molecule's conformation. Where the π-system of the bridge is out of plane relative to the pi systems of the electronic donor and acceptor (i.e., angle between 10° and 170°, or a range which is lesser or greater, such as between 30° to 150°), the molecule has a large HOMO/LUMO band gap; there is a tunneling distance across the bridge which can be significant (e.g., >1 nm). These features make the bridge effectively operate as an insulator.

When an external electronic field with an appropriate orientation is applied, however, the molecule will tend to polarize such that it is aligned with the electronic field. Maximum polarization is achieved where the bridge is coplanar with the other pi systems (i.e., angle between, for example, 0° and 10°, or a range which is slightly lesser or greater), since such an alignment allows facile electronic communication between each molecular section. This produces a more (e.g., highly) conductive state, relative to the state of effective operation as an insulator, with a much smaller band gap.

When an external electronic field of opposite polarity is applied to the molecule in its "on" state, electrostatic repulsion between the electronic field and the polarized molecular dipole forces the molecule to adopt a different conformation. The segments of the molecule—acceptor, donor, and bridge—turn relative to one another, which results in a non-planar alignment. Electronic communication between acceptor and donor segments is cut off, which prevents electron delocalization through the molecular system. Accordingly, the molecule is stable in this highly localized insulating state (i.e., "off" state) as well as in its highly conducting state (i.e., a bistable switch).

The "on" state of the switch permits an electron to easily tunnel into the molecular system through a short interface between an electrode and the electronic donor. The electron can subsequently travel through the delocalized orbitals of the molecular system and exit from the other end of the electrode to complete its path. In contrast, the tunneling current in an "off" state is essentially zero (i.e., $10^{-6}$ or smaller), and a higher voltage (e.g., 2.5 eV or more) can be used to inject an electron or hole into either the electronic donor or acceptor.

An aromatic ring system is a compound that has the ability to sustain an induced ring current. See Smith, M. B.; March, J. *March's Advanced Organic Chemistry*, 5$^{th}$ ed.; John Wiley & Sons, Inc.: New York, 2001; pp. 46-71, the disclosure of which is hereby incorporated by reference in its entirety. Examples of aromatic systems include, without limitation, the following: six-membered rings such as benzene and pyridine; five-membered ring systems such as pyrrole, thiophene and furan; polyaromatic compounds such as naphthalene, anthracene and pyrene; and, linked aromatic rings such as biphenyl.

Aromatic ring systems can be either substituted or unsubstituted. A substituted aromatic ring system possesses a chemical group covalently attached to it. Examples of chemical groups include, without limitation, linear alkyl, branched alkyl, cyclic alkyl, aromatic ring systems, substituted aromatic ring systems, electron donating groups, and electron withdrawing groups. Linear alkyl groups may be relatively small (e.g., $C_1$ to $C_6$), of medium length (e.g., $C_7$ to $C_{12}$), or larger (e.g., $C_{13}$ and above). Branched alkyl groups include, for example, isopropyl, isobutyl, and sec-butyl; and, cyclic alkyl groups include cyclopropyl, cyclobutyl, cyclopentyl, cyclohexyl, cycloheptyl, cyclooctyl and their substituted derivatives.

An electron donating group is group that can provide electron density to an aromatic ring system through electron delocalization, typically through a π-system. Examples of electron donating groups include, without limitation, —O—, —OH, —OR$_1$, —NH—, —NH$_2$, —NHR$_1$, —NR$_1$R$_2$, —PHR$_1$, —PR$_1$R$_2$, —S—, —SH, —SR$_1$, F, Cl, Br, and I. R$_1$ and R$_2$ are substituents independently selected from linear alkyl (e.g., methyl), branched alkyl, cyclic alkyl, and an aromatic ring system. The alkyl groups and aromatic ring systems may further be substituted with a variety of substituents (e.g, "clipping" substituents such as —SH, which binds to gold or silver substrates).

An electron withdrawing group is a group that can take electron density away from an aromatic system through electron delocalization, typically through a pi system. Examples of electron withdrawing groups include, without limitation, —C(=O)H, —C(=O)R$_3$, —C(=O)OR$_3$, —C(=O)OH, —CN, —N=O, —NO$_2$, —N=N—, CH=NR$_3$, —CR$_3$=NR$_4$, —C=C(CN)$_2$, —C=C(COR$_3$)$_2$, —C=C(CO$_2$R$_3$)$_2$, —C=C(COR$_3$)CO$_2$R$_4$, —SO$_2$OH, —SO$_2$OR$_3$, —S(=O)—R$_3$, —SO$_2$R$_3$, —BH$_2$, —BHR$_3$, —BR$_3$R$_4$, —PO$_3$H$_2$, —PO$_3$R$_3$R$_4$. R$_3$ and R$_4$ are substituents independently selected from linear alkyl (e.g., methyl), branched alkyl, cyclic alkyl, and an aromatic ring system. The alkyl groups and aromatic ring systems may further be substituted with a variety of substituents (e.g., "clipping" substituents such as —SH, which binds to gold or silver substrates).

The switchable bridge can be a pi system that can be switched on or off using an external electric field. The bridging group is either directly or indirectly connected to the electronic donor, electronic acceptor or both. It typically is an aromatic ring (e.g., phenyl), a single atom (e.g., —S—, —N—, —O—, —P—), or an atomic group (e.g., —C=C—, —CH$_2$C(O)—, —NHC(O)). When the group is an atomic group, it is switchable between an "on" state (i.e., conjugated state) and an "off" state (i.e., non-conjugated state) through tautomerization (e.g., —CH$_2$C(O)— to —CH=C(OH)— and —NH—C(O)— to —NH=C (OH)—). Examples of switchable bridges include, without limitation, —CH=CH—, —CH=CR$_5$—, —CR$_5$=CR$_6$—, —CH$_2$C(=O)— or —CH=C(OH)—, —CR$_5$HC(=O)— or —CR$_5$=C(OH)—, —CC—, —N=N—, —N=CH—, —NH—CO— or —N=C(OH)—, —N=C(NH$_2$)—, —N=C(SH)—, —NCS—, —NH—O— and —NHNH—. R$_5$ and R$_6$ are substituents independently selected from linear alkyl (e.g., methyl), branched alkyl, cyclic alkyl, and an aromatic ring system.

FIG. 1 shows an exemplary subclass of molecules (10) disclosed herein. The acceptor unit is designated as 11; the switchable bridge is designated as 12; and, the donor unit is designated as 13. "EWG" is the electron withdrawing group (e.g., —NO$_2$ or —CN), and "EDG" is the electron donating group (e.g., —NR$_1$R$_2$ where R$_1$ and R$_2$ are linear alkyl groups substituted with a "clipping" substituent). The units "G$_1$-G$_2$" and "G$_3$-G$_4$" are bridging groups as described in the preceding paragraph. Optional "adhering units" are shown as X$_1$ and X$_2$. The units provide for weak bi-stability (e.g., hydrogen bonding) between adjacent benzene rings and are independently selected from the following chemical groups: hydrogen; a heteroatom such as F, Cl, Br, and I; heteroatom containing functional groups such as —OH, —SH, or —NH$_2$; and substituted hydrocarbons. Variable position "Z" is an optional tuning atom, or atomic group, that can be used to tune the molecule's electronic properties. It is selected from a group of atomic units consisting of —CH=, —N=, —S—, —O—, and —P=.

Figure 2:
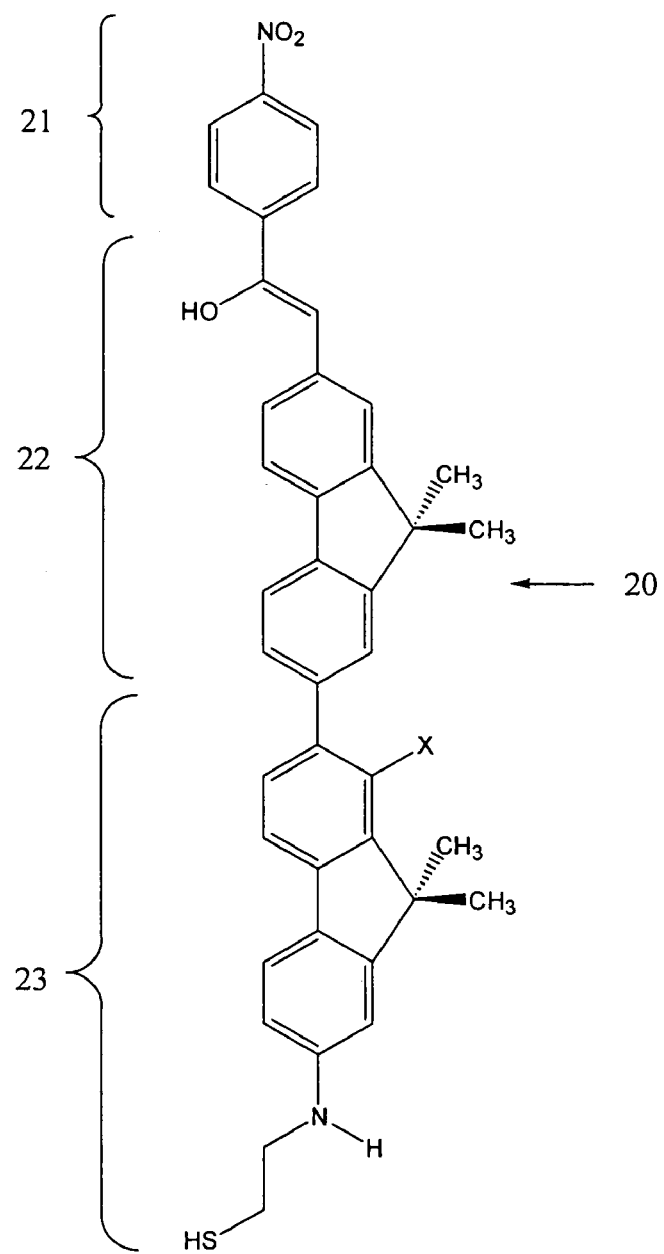
FIG. 2 shows a second exemplary subclass of molecules disclosed herein.

FIG. 2 shows another exemplary subclass of molecules (20). The acceptor unit is designated 21 and possesses an —NO$_2$ electron withdrawing group; the switchable bridge is designated 22 and includes the tautomerized (i.e., enol) form of a ketone; and the donor unit is designated 23 and contains an —NHR$_1$ group as an electron donating group. As with compound 11 described above, X is a "adhering unit."

Molecules disclosed herein can be synthesized using any suitable method. Organotransition metal cross-coupling reactions, however, are particularly useful for the production of the instant compounds.

Figure 3:
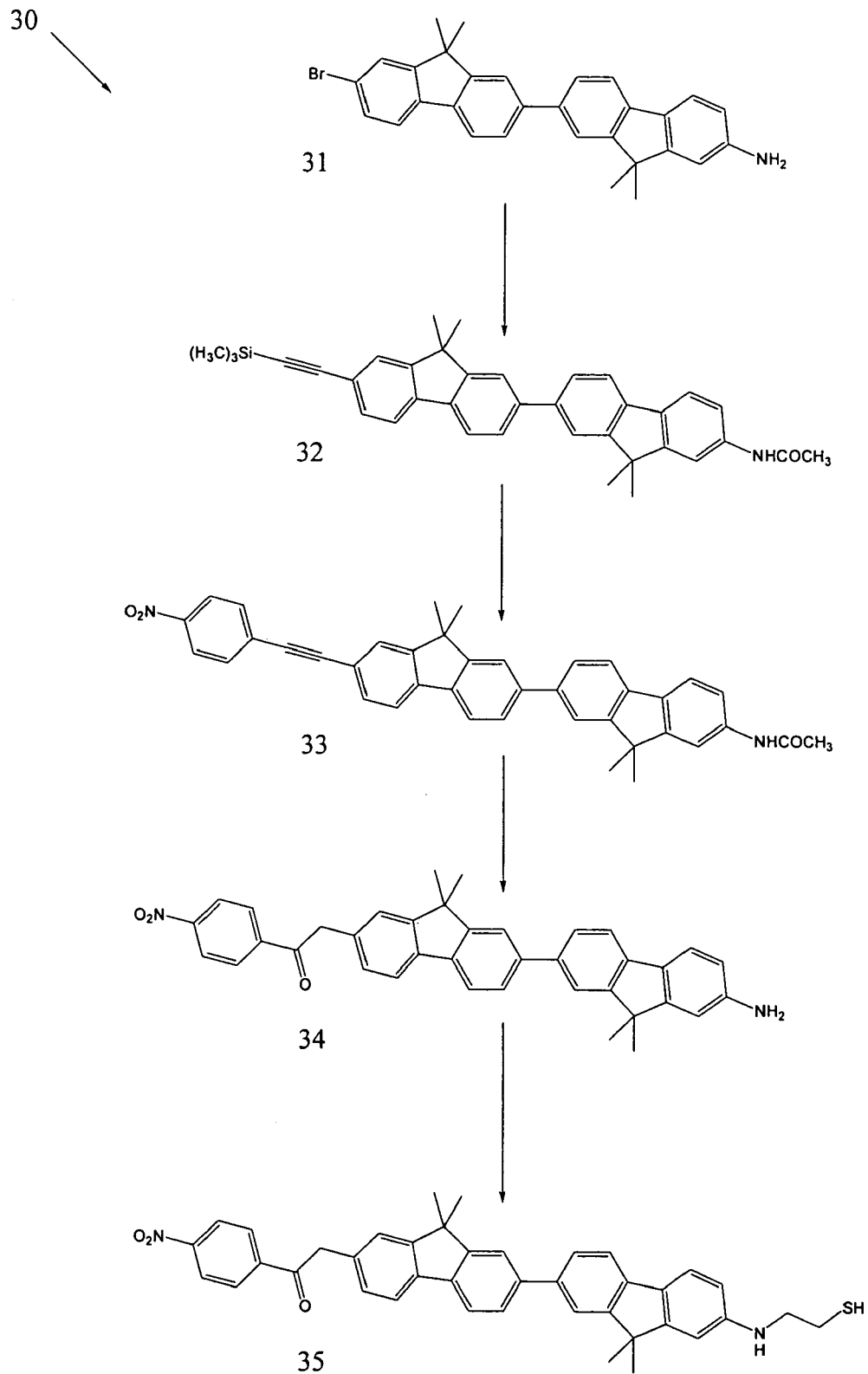
FIG. 3 shows an exemplary synthetic scheme for the production of a compound, where X is hydrogen.

FIG. 3 shows a synthetic scheme (30) for the production of compound 20 (FIG. 2), where X is hydrogen. Compound 31, 7'-bromo-9,9,9',9'-tetramethyl-9H,9'H-[2,2']bifluoreny-7-ylamine, is acetylated and subsequently coupled with trimethylsilylacetylene to provide N-(9,9,9',9'-tetramethyl-7'-trimethylsilanylethynyl-9H,9'H-[2,2']bifluorenyl-7-yl)-acetamide 32. Trimethylsilyl derivative 32 is subjected to an organometallic cross-coupling reaction in the presence of 4-iodo-nitrobenzene to afford N-[9,9,9',9'-tetramethyl-7'-(4-nitro-phenylethynyl)-9H,9'H-[2,2']bifluoreny-7-yl]-acetamide 33. Acetylene 33 is converted to ketone 34—2-(7'-amino-9,9,9',9'-tetramethyl)-9H,9'H-[2,2']bifluoreny-7-yl]-1-(4-nitro-phenyl)-ethanone—through the addition of H$_2$O, which also effects the hydrolysis of the terminal acetamide. Alkylation of 34 provides the desired compound 35, 2-[7'-(2-mercapto-ethylamino)-9,9,9',9'-tetramethyl-9H,9'H-[2,2']bifluoreny-7-yl]-1-(4-nitro-phenyl)-ethanone.

Figure 4:
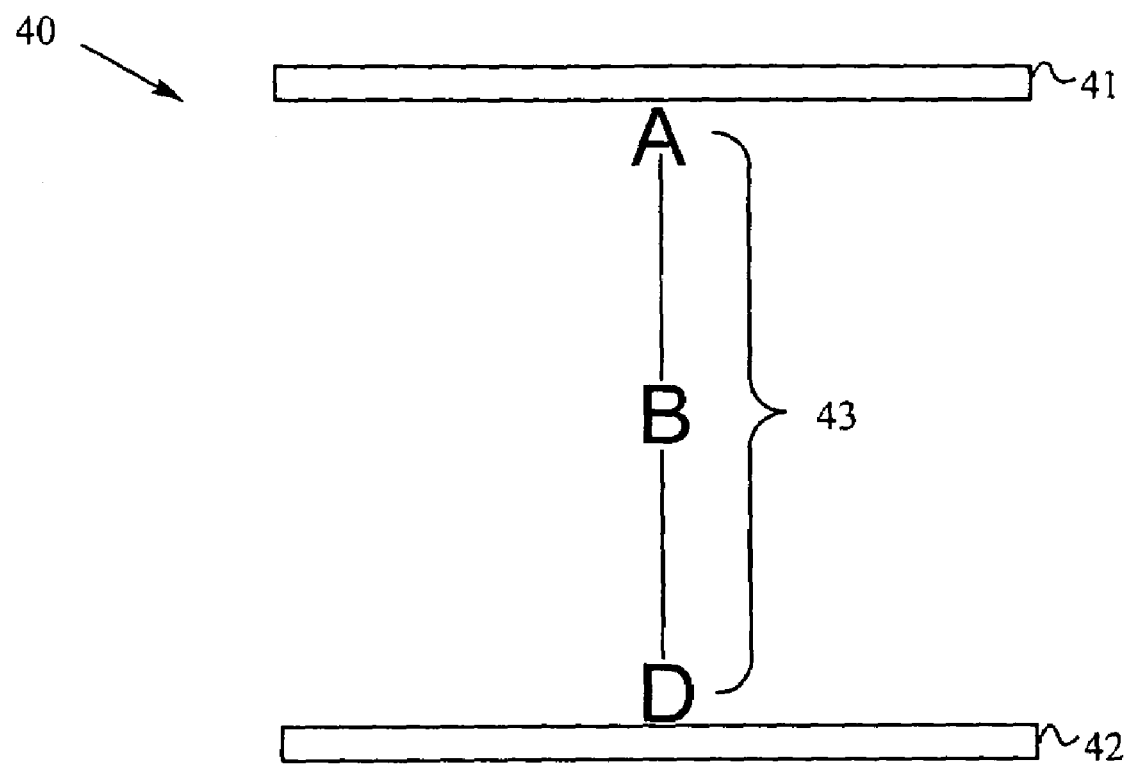
FIG. 4 illustrates an exemplary molecular switch using a generic compound disclosed herein.

Molecular switches containing compounds of the above-recited molecule classes are also described herein. FIG. 4 illustrates an exemplary switch (40) using a generic compound (43) disclosed herein. Compound 43 is placed between two terminals, 41 and 42, through which an electric field can be applied. The electronic acceptor "A" is proximal or connected to terminal 41, while the electronic donor "D" is proximal or connected to terminal 42.

Figure 5:
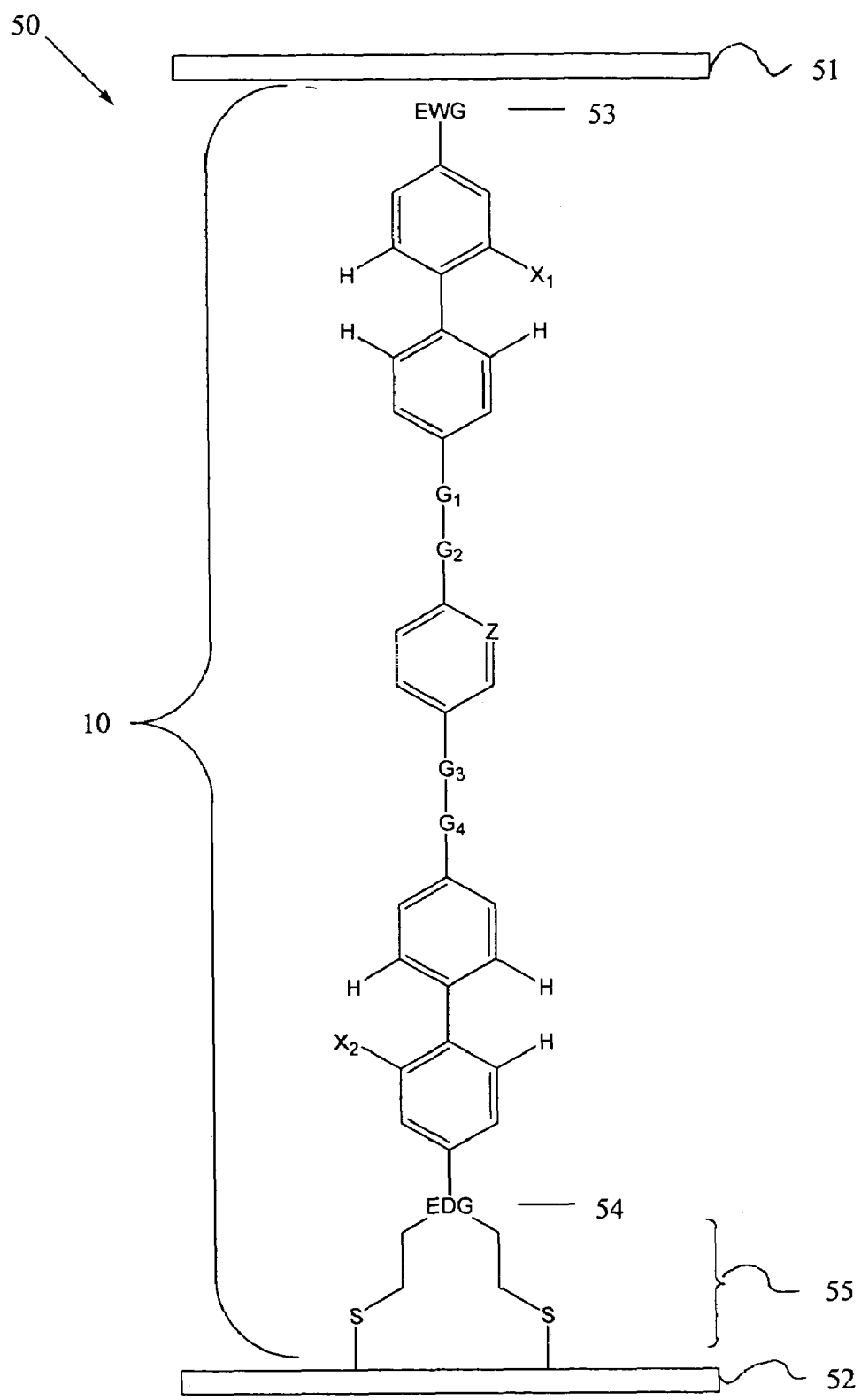
FIG. 5 illustrates an exemplary molecular switch that includes a molecule subclass.

The exemplary switch is further illustrated in FIG. 5, which shows the inclusion of molecule subclass 10 into the switch (50). Compound 10 is placed between two terminals, 51 and 52. The electronic acceptor 53 (i.e., EWG) is proximal to terminal 51. The electronic donor 54 (i.e., EDG) is attached to terminal 52 through "clipping" substituent 55. A clipping substituent refers to di-substituted mercaptoalkyl groups. It can be a di-substituted-2-mercaptoethyl group in the FIG. 5 example. Likewise, compound 20 can be placed between two electrodes.

Figure 6:
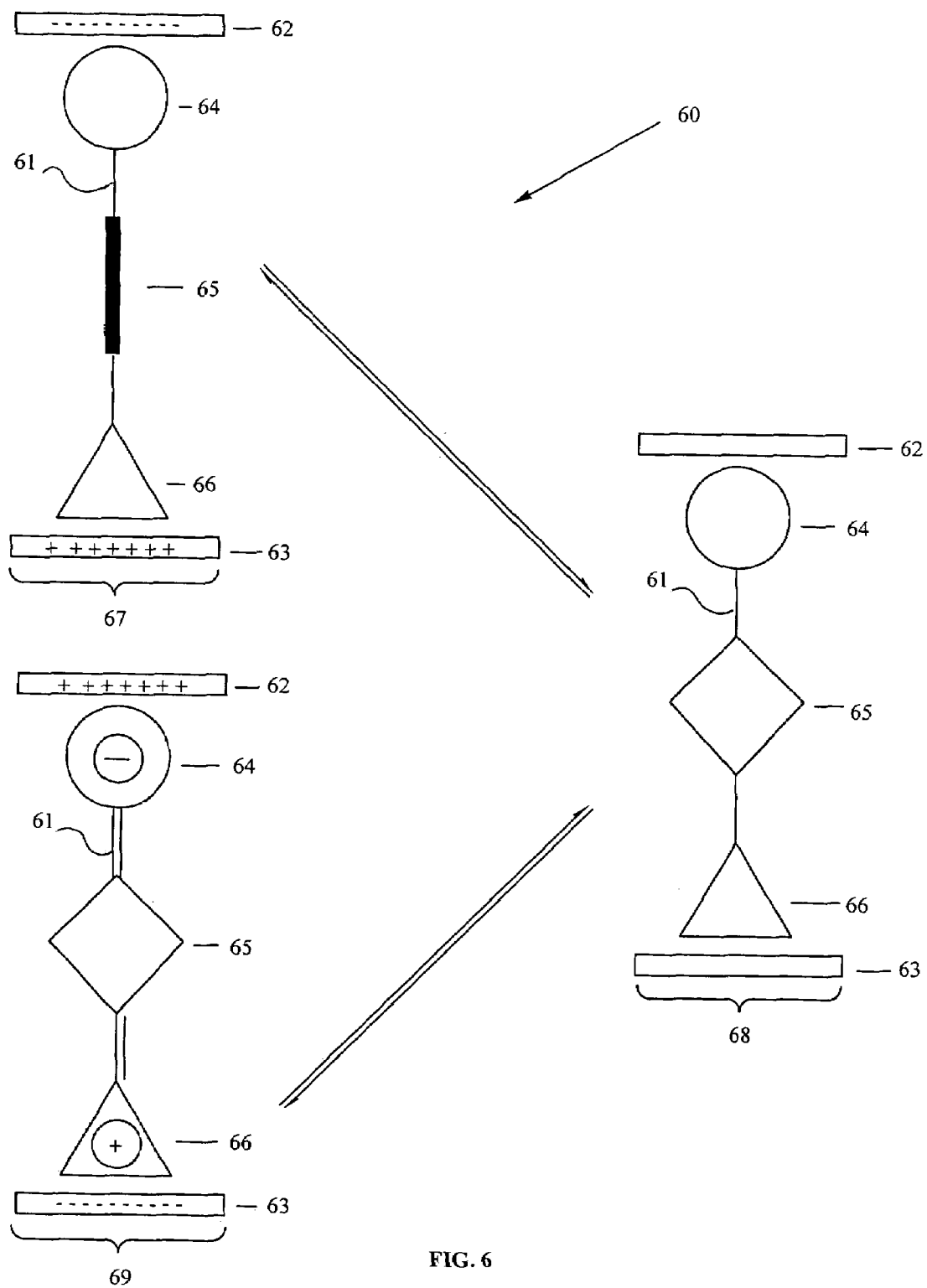
FIG. 6 illustrates an exemplary method of switching using a generic compound disclosed herein.

Methods of electronic switching can use compounds of the above-recited molecule classes. FIG. 6 illustrates such a method (60) using a generic compound disclosed herein (61). Compound 61 is placed between two terminals, 62 and 63. Element 64 is the electronic acceptor portion of 61; 65 is the bridge portion; and, 66 is the electronic donor portion. As shown in 67, the switch is in an "off" state (i.e., nonconducting): bridge 65 is out of plane, which inhibits electronic communication between 64 and 65. This is due to the presence of an electric field where terminal 62 is negatively charged and terminal 63 is positively charged. Conformation 68 is a transition state where each of compound 61's units are coplanar. In conformation 69, an electric field of opposite polarity to that of 67 is applied, producing an "on" state (i.e., conducting). Electronic communication among the three coplanar units of 61 results in polarization of the compound: acceptor portion 64 bears at least a partial negative charge while donor portion 66 bears at least a partial positive charge.

Figure 7:
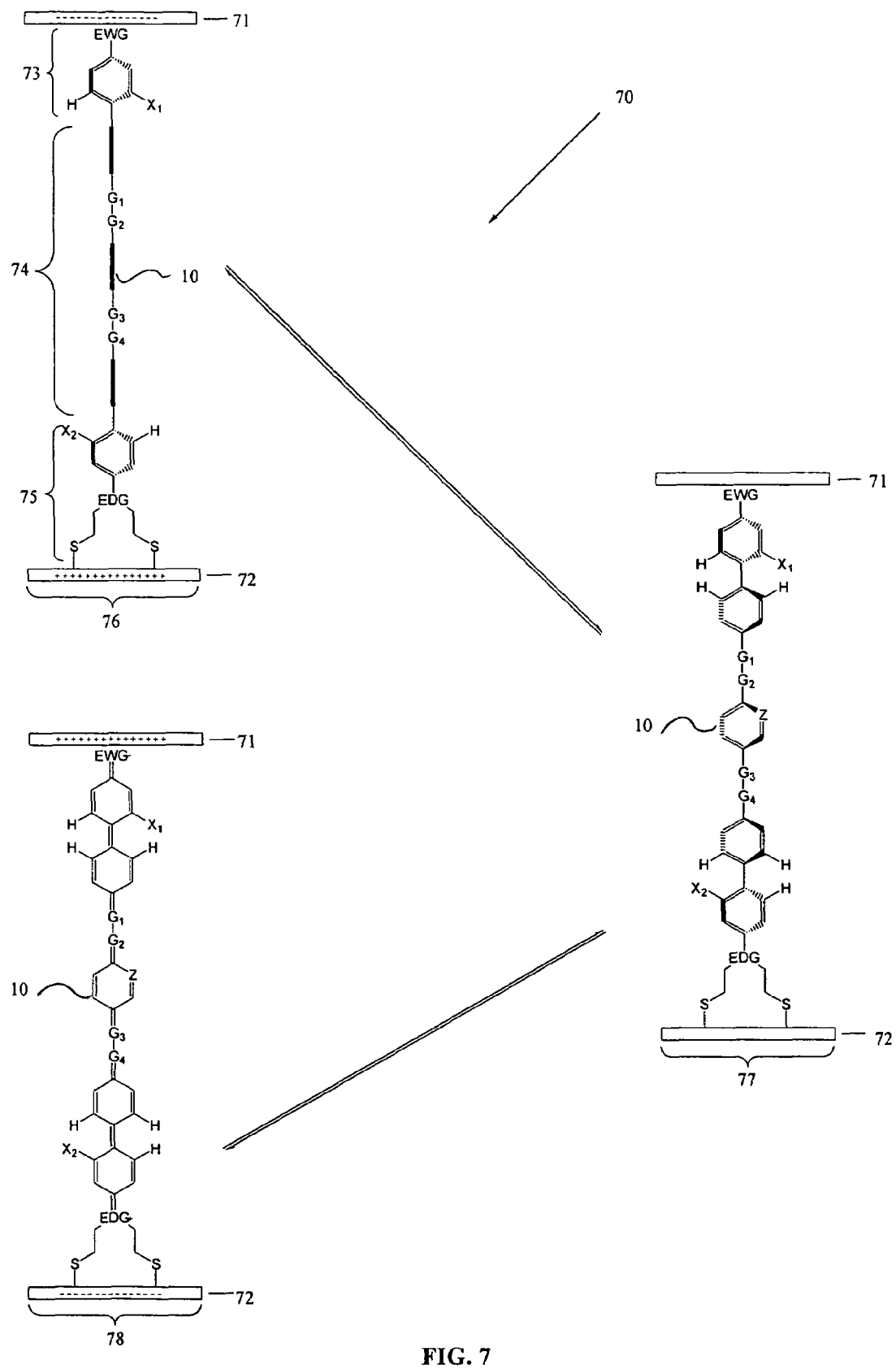
FIG. 7 illustrates an exemplary method of switching using a molecule class.
Figure 8:
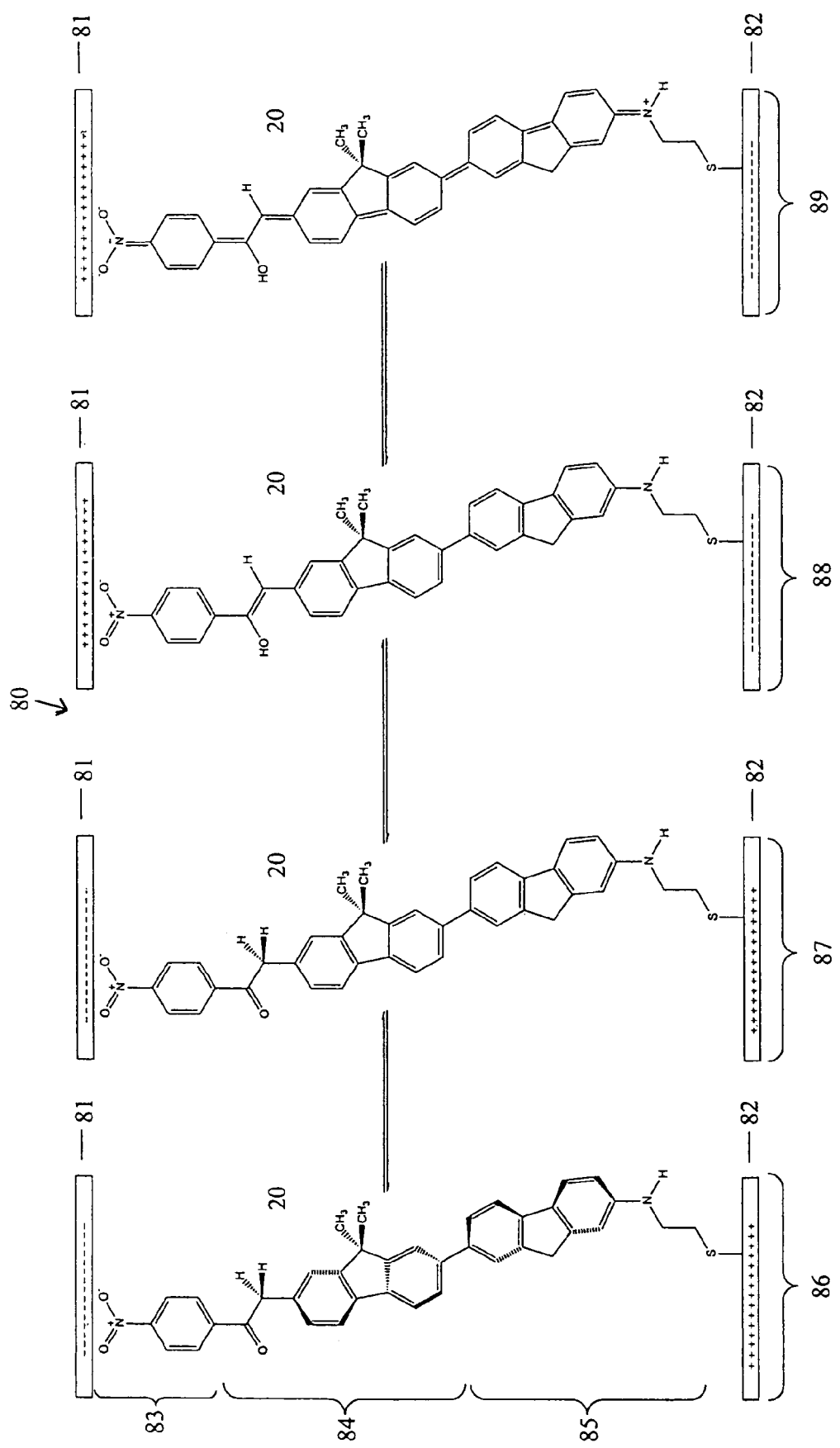
FIG. 8 illustrates an exemplary method where the compound of the molecular switch includes a switchable bridge.

A method of switching is further illustrated in reference to FIGS. 7 and 8. FIG. 7 illustrates the method using molecule class 10. Compound 10 is placed between two terminals, 71 and 72. Section 73 is the electron acceptor portion of 10, while sections 74 and 75 are the bridge and electron donor portions respectively. Conformation 76 represents the "off" stage for the switch; bridge portion 74 is out of plane, which inhibits electronic communication between 73 and 75. Conformation 77 is a transition state for the switch, where the bridging portion 74 is traveling toward planarity. Upon reaching substantial planarity, conformation 78 is produced and the switch is "on." This conformation allows molecular portions 73 and 74 to electronically communicate. Compound 10 polarizes, producing at least a partial negative charge on the electron withdrawing group (i.e., EWG) and at least a partial positive charge on the electron donating group (i.e., EDG).

FIG. 8 illustrates an exemplary method (80) where the compound of the molecular switch includes a switchable bridge. Compound 20 is placed between two terminals, 81 and 82. As shown in conformation 86—an "off" state where there is complete molecular depolarization—portion 83, bridge 84, and donor portion 85 are not coplanar; bridge 84 further contains a ketone moiety. Compound 20 comes to substantial coplanarity in conformation 87, but electronic communication throughout the molecule is inhibited since the ketone moiety interrupts the communication pathway (i.e., π-system). Providing an electric field of opposite polarity, as in conformation 88, induces tautomerization of the ketone to produce an enol. The produced, continuous pi system in the presence of the electric field effects complete compound polarization (89).

The molecular switches disclosed herein can be used to produce electronic devices that possess functional length scales measured in nanometers. This ability is the direct result of the molecules, switches and methods described above.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:
1. A compound of a structure:

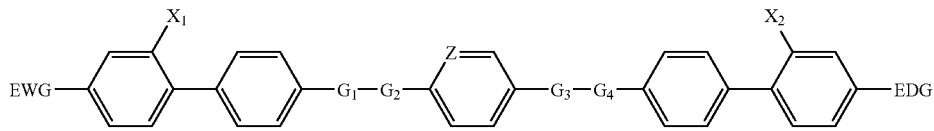

wherein "EWG" is selected from the group consisting of —C(=O)H, —C(=O)R$_3$, —C(=O)OR$_3$, —C(=O)OH, —CN, —N=O, —NO$_2$, —N=N—, —CH=NR$_3$, —CR$_3$=NR$_4$, —C=C(CN)$_2$, —C=C(COR$_3$)$_2$, —C=C(CO$_2$R$_3$)$_2$, —C=C(COR$_3$)CO$_2$R$_4$, —SO$_2$OH, —SO$_2$OR$_3$, —S(=O)—R$_3$, —SO$_2$R$_3$, —BH$_2$, —BHR$_3$, —BR$_3$R$_4$, —PO$_3$H$_2$, and —PO$_3$R$_3$R$_4$, wherein R$_3$ and R$_4$ are substituents independently selected from linear alkyl, branched alkyl, cyclic alkyl, and an aromatic ring system, and wherein the alkyl substituents are substituted or unsubstituted;

"EDG" is selected from the group consisting of —O$^-$, —OH, —OR$_1$, —NH$^-$, —NH$_2$, —NHR$_1$, —NR$_1$R$_2$, —PHR$_1$, —PR$_1$R$_2$, —S$^-$, —SH, —SR$_1$, F, Cl, Br, and I, wherein R$_1$ and R$_2$ are substituents independently selected from linear alkyl, branched alkyl, cyclic alkyl, and an aromatic ring system, and wherein the alkyl substituents are substituted or unsubstituted;

X$_1$ and X$_2$ are independently selected from the group consisting of hydrogen, F, Cl, Br, and I, —OH, —SH, —NH$_2$; and substituted alkyl groups;

G$_1$-G$_2$ and G$_3$-G$_4$ are independently selected from the group consisting of —CH=CH—, —CH=CR$_5$—, —CR$_5$=CR$_6$—, —CH$_2$C(=O)—, —CR$_5$HC(=O)—, —CC—, —N=N—, —N=CH—, —NH—CO—, —N=C(NH$_2$)—, —N=C(SH)—, —NCS—, —NH—O— and —NHNH—, wherein R$_5$ and R$_6$ are substituents independently selected from linear alkyl, branched alkyl, cyclic alkyl, and an aromatic ring system, and wherein the alkyl substituents are substituted or unsubstituted; and, Z is —CH=.

2. The compound according to claim 1, wherein "EWG" is selected from the group consisting of —C(=O)H, —C(=O)R$_3$, —C(=O)OR$_3$, —C(=O)OH, —CN, —N=N—, CH=NR$_3$, —CR$_3$=NR$_4$, —C=C(CN)$_2$, —C=C(COR$_3$)$_2$, —C=C(CO$_2$R$_3$)$_2$, —C=C(COR$_3$)CO$_2$R$_4$, and —NO$_2$.

3. The compound according to claim 2, wherein "EDG" is selected from the group consisting of —OH, —OR$_1$, —NH$_2$, —NHR$_1$, —NR$_1$R$_2$, —PHR$_1$, —PR$_1$R$_2$, —SH, and —SR$_1$.

4. The compound according to claim 3, wherein X$_1$ and X$_2$ are independently selected from the group consisting of hydrogen, F, Cl, Br, I and OH.

5. The compound according to claim 4, wherein G$_1$-G$_2$ and G$_3$-G$_4$ are independently selected from the group consisting of —CH=CH—, —CH=CR$_5$—, —CR$_5$=CR$_6$—, —CH$_2$C(=O)—, —CR$_5$HC(=O)—, —CC—, —N=N—, —N=CH—, and —NH—CO—.

6. The compound according to claim 1, wherein "EDG" is selected from the group consisting of —OH, —OR$_1$, —NH$_2$, —NHR$_1$, —NR$_1$R$_2$, —PHR$_1$, —PR$_1$R$_2$, —SH, and —SR$_1$.

7. The compound according to claim 1, wherein X$_1$ and X$_2$ are independently selected from the group consisting of hydrogen, F, Cl, Br, I and OH.

8. The compound according to claim 1, wherein G$_1$-G$_2$ and G$_3$-G$_4$ are independently selected from the group consisting of —CH=CH—, —CH=CR$_5$—, —CR$_5$=CR$_6$—, —CH$_2$C(=O)—, —CR$_5$HC(=O)—, —CC—, —N=N—, —N=CH—, and —NH—CO—.

* * * * *